(12) United States Patent
Meskens et al.

(10) Patent No.: US 10,207,117 B2
(45) Date of Patent: Feb. 19, 2019

(54) WIRELESS COMMUNICATION IN AN IMPLANTABLE MEDICAL DEVICE SYSTEM

(71) Applicant: Cochlear Limited, Macquarie University, NSW (AU)

(72) Inventors: Werner Meskens, Mechelen (BE); Koen Van Herck, Kontich (BE)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 15/157,626

(22) Filed: May 18, 2016

(65) Prior Publication Data

US 2017/0028200 A1    Feb. 2, 2017

Related U.S. Application Data

(60) Provisional application No. 62/198,227, filed on Jul. 29, 2015.

(51) Int. Cl.
*A61N 1/36* (2006.01)
*A61N 1/372* (2006.01)

(52) U.S. Cl.
CPC ..... *A61N 1/37223* (2013.01); *A61N 1/36036* (2017.08); *A61N 1/37252* (2013.01)

(58) Field of Classification Search
CPC ............ A61N 1/36038; A61N 1/36036; A61N 1/37223; A61N 1/36032
See application file for complete search history.

(56) References Cited

U.S. PATENT DOCUMENTS

| 5,601,617 A | 2/1997 | Loeb et al. |
| 5,603,726 A | 2/1997 | Schulman et al. |
| 5,824,022 A | 10/1998 | Zilberman et al. |

(Continued)

FOREIGN PATENT DOCUMENTS

| EP | 2747458 A1 | 6/2014 |
| KR | 10-2013-0133790 A | 12/2013 |
| WO | 2008092182 A1 | 8/2008 |

OTHER PUBLICATIONS

S. K. An et al., "Design for a Simplified Cochlear Implant System," in IEEE Transactions on Biomedical Engineering, vol. 54, No. 6, pp. 973-982, Jun. 2007. doi: 10.1109/TBME.2007.895372.

(Continued)

*Primary Examiner* — Paula J Stice
(74) *Attorney, Agent, or Firm* — Edell, Shapiro & Finnan, LLC

(57) ABSTRACT

Embodiments presented herein are generally directed to techniques for the transfer of isochronous stimulation data over a standardized isochronous audio or data link between components of an implantable medical device system. More specifically, as described further below, a first component is configured to generate dynamic stimulation data based on one or more received sound signals. The first component is configured to obtain static configuration data and to encode the dynamic stimulation data and the static configuration data into a series of isochronous wireless packets. The first component is configured to transmit the series of wireless packets over an isochronous wireless channel to a second component of the implantable medical device system.

23 Claims, 6 Drawing Sheets

(56) References Cited

U.S. PATENT DOCUMENTS

| | | |
|---|---|---|
| 6,002,966 A | 12/1999 | Loeb et al. |
| 6,219,580 B1 | 4/2001 | Faltys et al. |
| 8,849,202 B2 | 9/2014 | Linde et al. |
| 2007/0203547 A1* | 8/2007 | Costello ................. A61N 1/056 607/59 |
| 2008/0031478 A1 | 2/2008 | Alber et al. |
| 2011/0069853 A1 | 3/2011 | Kulkarni et al. |
| 2012/0041515 A1 | 2/2012 | Meskens et al. |
| 2013/0090517 A1 | 4/2013 | Van den Heuvel et al. |
| 2014/0146985 A1 | 5/2014 | Mishra et al. |
| 2015/0023536 A1 | 1/2015 | Scheller |

OTHER PUBLICATIONS

Patrick, James F., Peter A. Busby, and Peter J. Gibson. "The development of the Nucleus Freedom cochlear implant system." Trends in amplification 10.4 (2006): 175-200.

F. G. Zeng, S. Rebscher, W. Harrison, X. Sun and H. Feng, "Cochlear Implants: System Design, Integration, and Evaluation," in IEEE Reviews in Biomedical Engineering, vol. 1, pp. 115-142, 2008. doi: 10.1109/RBME.2008.2008250.

Extended European Search Report in corresponding EP Application No. 16829939.4, dated Dec. 27, 2018, 6 pages.

* cited by examiner

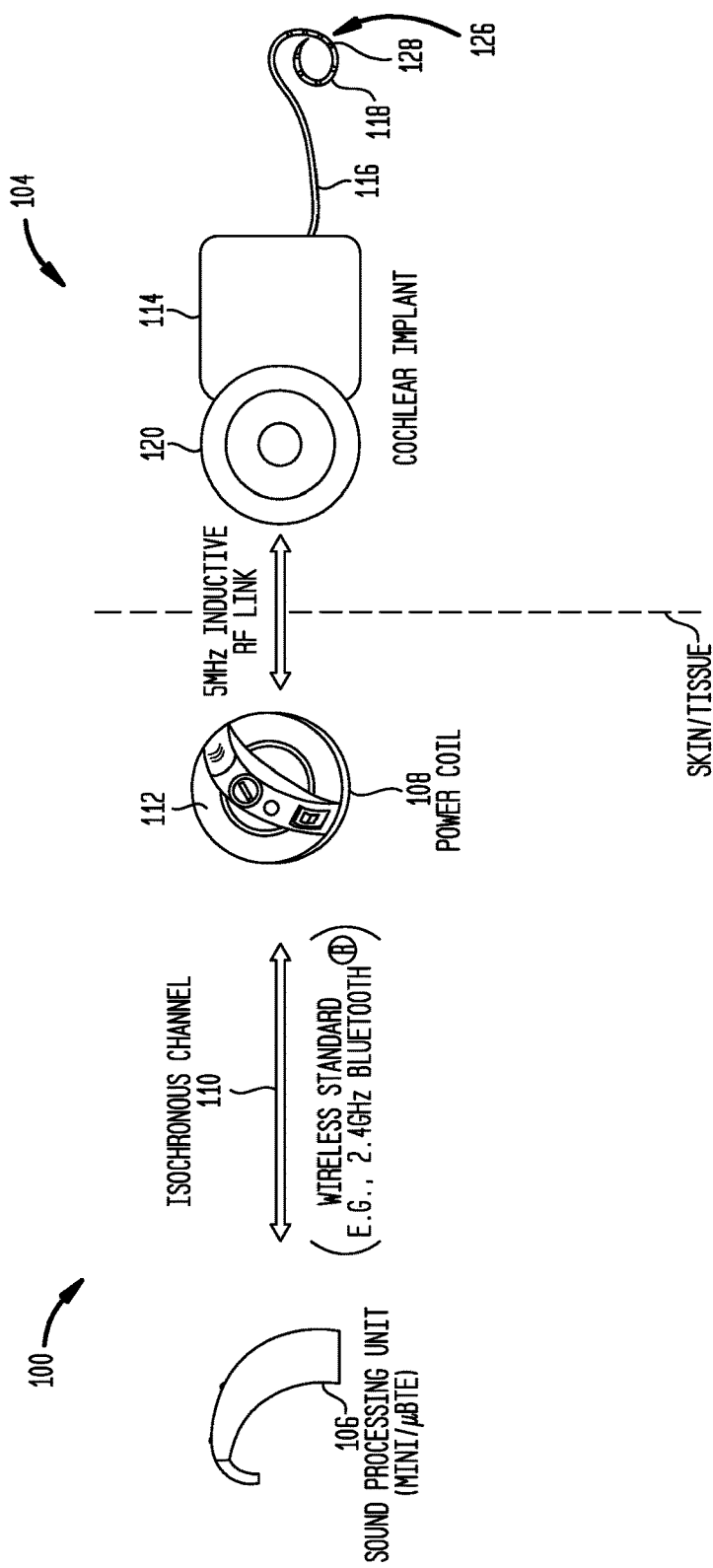

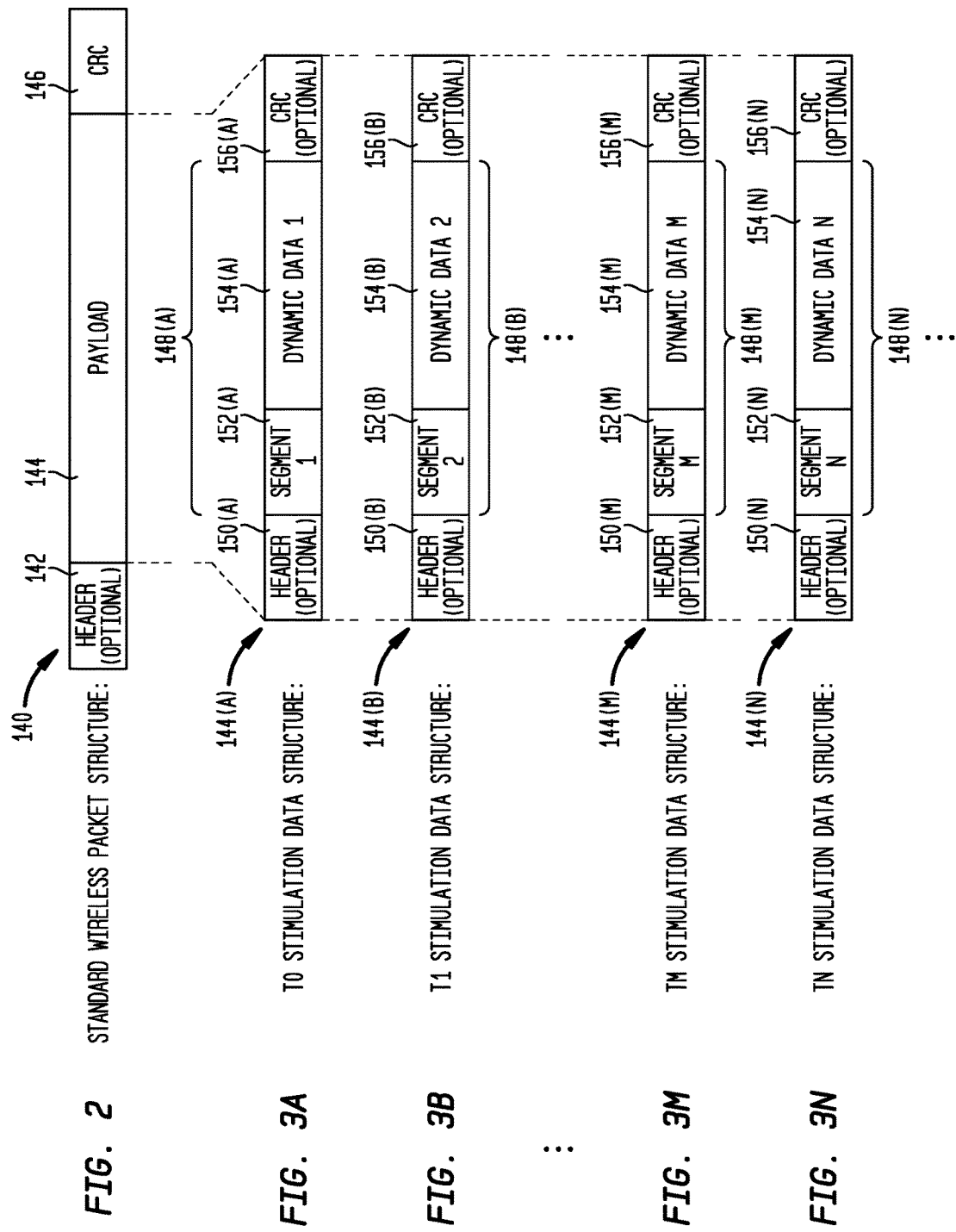

| BYTE # | 0 | 1 | 2 | 3 | 4 | ... | 9 | 10 | 11 |
|---|---|---|---|---|---|---|---|---|---|
| FRAME # | SYNC | STIMULUS CHANNELS | | STIMULUS LEVELS | | | | | |
| 0 | 1 | 22-17 | 16-9 | 8-1 | | | | | DATA |
| 1 | 0 | 22-17 | 16-9 | 8-1 | STIM 1 | STIM 2 | ... | STIM 7 | STIM 8 | DATA 0 |
| 2 | 0 | 22-17 | 16-9 | 8-1 | STIM 1 | STIM 2 | ... | STIM 7 | STIM 8 | DATA 1 |
| ... | 0 | 22-17 | 16-9 | 8-1 | STIM 1 | STIM 2 | ... | STIM 7 | STIM 8 | DATA 2 |
| 30 | 0 | 22-17 | 16-9 | 8-1 | STIM 1 | STIM 2 | ... | STIM 7 | STIM 8 | ... |
| 31 | 0 | 22-17 | 16-9 | 8-1 | STIM 1 | STIM 2 | ... | STIM 7 | STIM 8 | DATA 30 |
| 32 | 1 | 22-17 | 16-9 | 8-1 | STIM 1 | STIM 2 | ... | STIM 7 | STIM 8 | DATA 31 |
| 33 | 0 | 22-17 | 16-9 | 8-1 | STIM 1 | STIM 2 | ... | STIM 7 | STIM 8 | DATA 0 |
| 34 | 0 | 22-17 | 16-9 | 8-1 | STIM 1 | STIM 2 | ... | STIM 7 | STIM 8 | DATA 1 |
| ... | 0 | 22-17 | 16-9 | 8-1 | STIM 1 | STIM 2 | ... | STIM 7 | STIM 8 | DATA 2 |
| | | | | | | | | | ... |

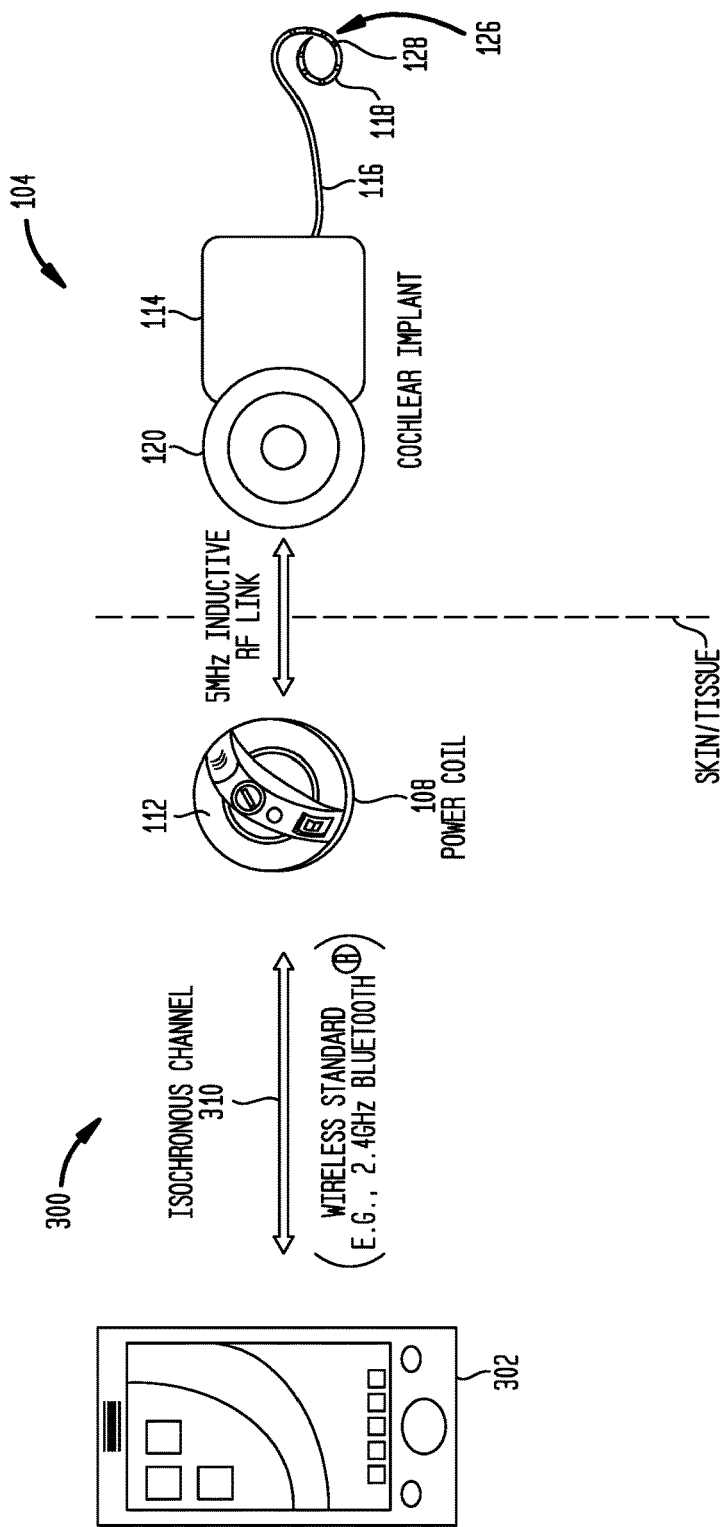

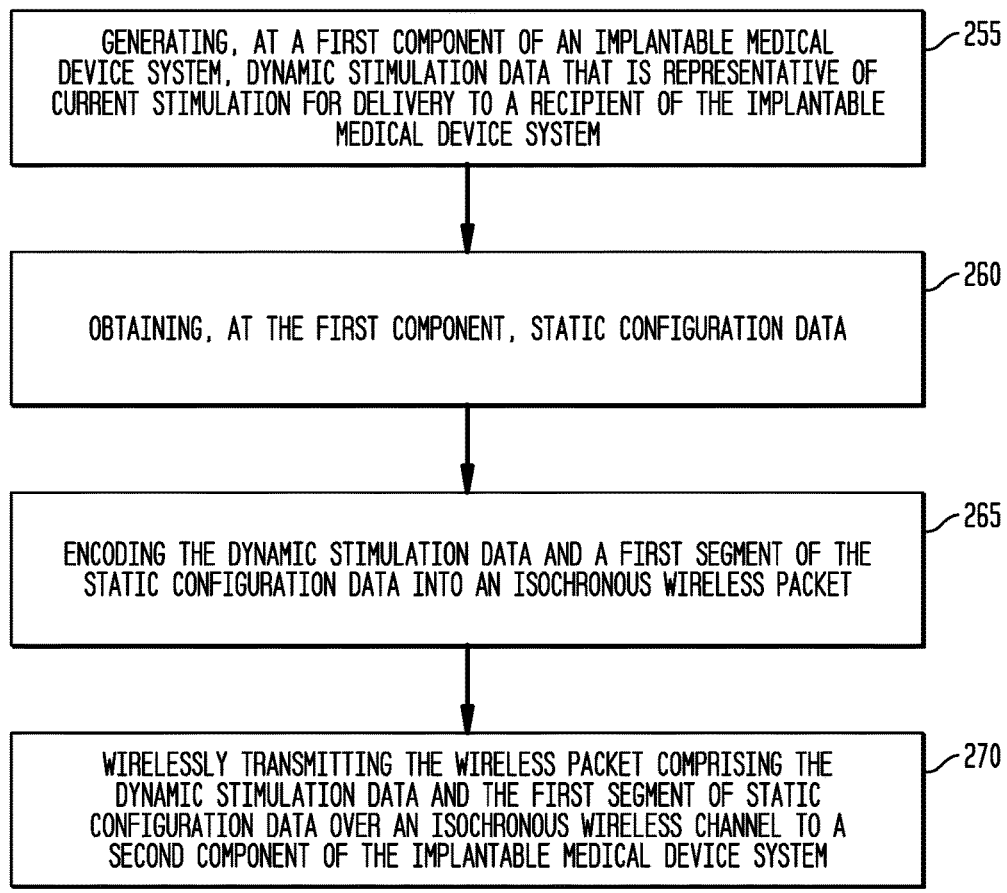

WIRELESS COMMUNICATION IN AN IMPLANTABLE MEDICAL DEVICE SYSTEM

CROSS REFERENCE TO RELATED APPLICATIONS

This application claims priority to U.S. Provisional Application No. 62/198,227 entitled "Wireless Communication in an Implantable Medical Device System," filed Jul. 29, 2015, the content of which is hereby incorporated by reference herein.

BACKGROUND

Field of the Invention

The present invention relates generally to a wireless communication in an implantable medical device system.

Related Art

Implantable medical device systems, which include one or more implantable components, have provided a wide range of therapeutic benefits to recipients over recent decades. The types of implantable medical device systems and the ranges of functions performed thereby have increased over the years. For example, many implantable medical device systems now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

There are several types of implantable medical device systems that operate by delivering electrical stimulation (current stimulation) to the nerves, muscle or other tissue fibers of a recipient. These implantable medical device systems, sometimes referred to herein as implantable tissue-stimulating systems, typically deliver current stimulation to compensate for a deficiency in the recipient. For example, tissue-stimulating hearing systems are often proposed when a recipient experiences sensorineural hearing loss due to, for example, the absence or destruction of the cochlear hair cells that transduce acoustic signals into nerve impulses or when a recipient experiences sensorineural hearing loss due to damage to the auditory nerve.

SUMMARY

In one aspect, a method is provided. The method comprises: generating, at a first component of an implantable medical device system, dynamic stimulation data representing current stimulation for delivery to a recipient of the implantable medical device system; obtaining, at the first component, static configuration data; encoding the dynamic stimulation data and a first segment of the static configuration data into an isochronous wireless packet; and transmitting the wireless packet comprising the dynamic stimulation data and the first segment of static configuration data over an isochronous wireless channel to a second component of the implantable medical device system.

In another aspect, a method is provided. The method comprises receiving a plurality of sound signals; generating a plurality of sets of dynamic stimulation data based on the sound signals, wherein the dynamic stimulation data represents at least the intensity and location of current stimulation pulses that, when delivered to a recipient, will evoke perception of the sound signals by the recipient; obtaining static configuration data defining one or more recipient-specific aspects of the current stimulation pulses; segmenting static configuration data into a plurality of discrete static configuration data segments; and wirelessly streaming each of the plurality of static configuration data segments with one of the plurality of sets of dynamic stimulation data over an isochronous channel in a serialized and repetitive manner.

In another aspect an external component of a tissue-stimulating hearing system is provided. The external component comprises: a sound processor configured to generate dynamic stimulation data based on one or more received sound signals, wherein the dynamic stimulation data represents at least the intensity and location of current stimulation pulses that, when delivered to a recipient, will evoke perception of the sound signals by the recipient; and a wireless transceiver configured to: obtain static configuration data defining one or more recipient-specific aspects of the current stimulation pulses, encode the dynamic stimulation data and a first segment of the static configuration data into an isochronous wireless packet, and transmit the wireless packet comprising the dynamic stimulation data and the first segment of static configuration data over an isochronous wireless channel to a second component of the tissue-stimulating hearing system.

BRIEF DESCRIPTION OF THE DRAWINGS

Embodiments of the present invention are described herein in conjunction with the accompanying drawings, in which:

FIG. 1 is a schematic diagram illustrating a cochlear implant system in accordance with embodiments presented herein;

FIG. 2 is a schematic diagram of a standardized wireless packet into which dynamic stimulation data and static configuration data are encoded, in accordance with embodiments presented herein;

FIGS. 3A-3N are a series of schematic diagrams illustrating the encoding of dynamic stimulation data and static configuration data into a wireless packet, in accordance with embodiments presented herein;

FIG. 6 is a schematic diagram of another cochlear implant system in accordance with embodiments presented herein; and FIG. 7 is a flowchart illustrating an example method for the transfer of isochronous stimulation data over a standardized audio link, in accordance with embodiments presented herein.

DETAILED DESCRIPTION

Figure 4:
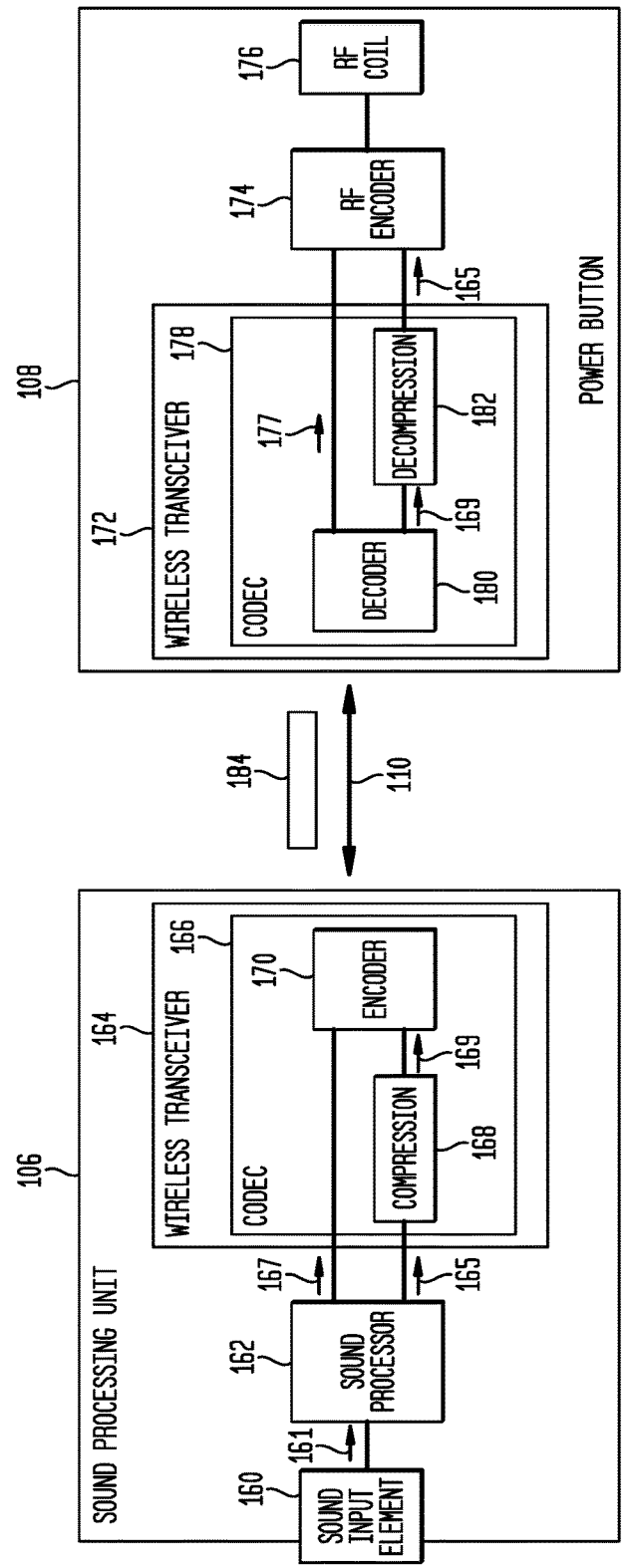
FIG. 4 is a functional block diagram of a cochlear implant system in accordance with embodiments presented herein.

Embodiments presented herein are generally directed to techniques for the transfer of isochronous stimulation data over a standardized audio link between components of an implantable medical device system. More specifically, as described further below, a first component is configured to generate dynamic stimulation data based on one or more received sound signals. The first component is configured to obtain static configuration data and to encode the dynamic stimulation data and the static configuration data into a series of isochronous wireless packets. The first component is configured to transmit the series of wireless packets over an isochronous wireless channel to a second component of the implantable medical device system.

There are several types of implantable tissue-stimulating systems that operate by delivering stimulation to a recipient so as to compensate for a deficiency in the recipient's nerves, tissue, etc. Merely for ease of illustration, the techniques presented herein are primarily described herein with reference to one type of implantable tissue-stimulating system, namely a cochlear implant system. It is to be appreciated that techniques presented herein may be used with other implantable tissue-stimulating systems that include, for example, auditory brainstem stimulators, implantable pacemakers, defibrillators, functional electrical stimulation devices, pain relief stimulators, visual prostheses, other neural or neuromuscular stimulators, etc.

FIG. 1 is schematic diagram of an exemplary cochlear implant system 100 configured to implement embodiments of the present invention. The cochlear implant system 100 comprises first and second external components 106 and 108 and an implantable component 104. In this example, the implantable component 104 is a cochlear implant.

In the illustrative embodiment of FIG. 1, the first external component 106 is a sound processing unit and the external component 108 is a power button. As shown, the sound processing unit 106 is a behind-the-ear (BTE) unit, such as a mini or micro-BTE, configured to be attached to and worn adjacent to the recipient's ear. The power button 108 is a component having a generally cylindrical shape and is configured to be magnetically coupled to recipient at the same location as where an external coil is traditionally located.

As described further below, the power button 108 comprises a wireless transceiver for wireless communication with the sound processing unit 106 over a channel operated in accordance with a short-range wireless standard (i.e., a non-closely coupled wireless link), an external radio frequency (RF) coil 112, a magnet fixed relative to the external coil, and at least one rechargeable battery, such as an integrated or removable lithium-ion (LiIon) battery. The sound processing unit 106 comprises, or is connected to, among other elements, one or more sound input elements (e.g., microphones, telecoils, etc.) for detecting sound signals (sounds). The sound processing unit 106 also comprises a wireless transceiver for wireless communication with, for example, the power button 108 or other devices/components, and a sound processor over a wireless channel operated in accordance with a short-range wireless standard (i.e., a non-closely coupled wireless link). As described further below, the sound processor is configured to convert the sound signals received from the sound input element(s) into encoded data signals that represent the intensity and location (i.e., the cochlea location) of current stimulation pulses that, when delivered by cochlear implant 104, will evoke perception of the sound signals by the recipient. Since these encoded data are used by the cochlear implant 104 to generate current stimulation, and because these signals vary dynamically according to the sound signals, the encoded data signals generated by the sound processor are referred to herein as "dynamic stimulation data." In other words, the dynamic stimulation data is derived from the audio data by applying a speech processing/compressing/coding algorithm with a "map" containing certain fitting parameters. Also as described below, the dynamic stimulation data is wirelessly transferred from the sound processing unit 106 to the power button 108 for subsequent transcutaneous transmission to the cochlear implant 104 via an isochronous wireless link 110.

The cochlear implant 104 comprises an implant body 114, a lead region 116, and an elongate intra-cochlear stimulating assembly 118. The implant body 114 comprises an internal RF coil 120, a magnet fixed relative to the internal coil, an internal receiver/transceiver unit, sometimes referred to herein as internal transceiver unit, and a stimulator unit. The internal transceiver unit is electrically connected to the internal coil via one or more wires.

The magnets in the power button 108 and the implant body 114 facilitate the operational alignment of the external coil 112 in the power button with the internal coil 120 in the implant body. The operational alignment of the coils 112 and 120 enables the internal coil to trancutaneously receive power and data from the external coil over a closely-coupled RF link. The external and internal coils 112 and 120 are typically wire antenna coils.

Elongate stimulating assembly 118 is configured to be at least partially implanted in the cochlea of a recipient and includes a plurality of intra-cochlear stimulating contacts 128. The stimulating contacts 128 collectively form a contact array 126 and may comprise electrical contacts and/or optical contacts. Stimulating assembly 118 extends through an opening in the cochlea (e.g., cochleostomy, the round window, etc.) and has a proximal end connected to the stimulator unit in implant body 114 via lead region 116 that extends through the recipient's mastoid bone.

Standardized isochronous wireless channels/links, such as Bluetooth®, support multiple audio codec formats for voice and music (e.g., CVSD, PCM, (m)SBC, etc.). Bluetooth® is a registered trademark owned by the Bluetooth® SIG. In a standardized isochronous wireless channel, the user may have access to a transparent transport interface for one or more isochronous data channels at a certain frame size (e.g., 32 bits) and bitrate (e.g., 96 kilobits/second (kbps)).

As noted above, FIG. 1 illustrates a system in which a behind-the-ear (BTE) sound processing unit 106 (e.g., a micro-BTE) wirelessly communicates with the power button 108. However, sound processing units in accordance with embodiments presented herein may have a number of different arrangements. For example, in one alternative embodiment, the sound processing unit could be an in-the-canal unit that is configured to be located in the recipient's ear canal which is linked with an isochronous channel to a power button and/or to an implant.

Regardless of the location, form, and/or arrangement of the sound processing unit 106, the sound processing is performed in the sound processing unit 106 (i.e., the sound processing unit 106 is the centralized device of the system 100). As such, a reliable and secure standardized wireless channel is needed for wireless communication between the sound processing unit 106 and the power button 108. Therefore, presented herein are techniques to transfer dynamic stimulation data from the sound processing unit 106 to the power button 108 over a standardized wireless channel, such as a standardized protocol operating over wireless channels in the license-free 2.4 Gigahertz (GHz) band (e.g., a channel operated in accordance with the standard Bluetooth® protocol or any other wireless streaming standard providing a secure data stream over an isochronous channel). Such isochronous channels can be made reliable as they may be based upon acknowledgment (ACK) signals sent via a backlink from the power button to the sound processing unit.

In accordance with the embodiments presented herein, the sound processing unit 106 comprises a codec that is specifically designed and configured to compress or otherwise adapt dynamic stimulation data to the frame format, frame length and frame rate made available by a wireless transport interface (i.e., available on a standardized wireless channel). In other words, the codec in the sound processing unit 106 identifies the wireless packet/frame format for the standardized wireless channel and then encodes or maps the dynamic stimulation data into the available frame format.

Furthermore, in accordance with embodiments presented herein, the codec in the sound processing unit 106 is configured to embed segments of "static configuration data" into the wireless packets along with each of a plurality of sets of the dynamic stimulation data. More specifically, as noted above, the dynamic stimulation data (i.e., encoded data signals) represent the intensity and location of current stimulation pulses for delivery via cochlear implant 104. However, there are a variety of other pre-determined recipient-specific "static" parameters that dictate other aspects of current stimulation for a particular recipient. These parameters include, for example, channel-to-electrode mappings, pulse rate, pulse timing (electrical pulse width and inter-pulse gap), mode of stimulation (polarity, reference electrode), compression law or compression settings, amplitude mappings, etc. Amplitude mapping refers to the mapping of a sound intensity to a current level that is between the recipient's threshold (T) level (i.e., the level at which he/she can just hear the stimulus) and the maximum comfortable (C) level. In general, the static configuration data is data indicating how the dynamic stimulation data is to be used for generation of current pulses for delivery to the recipient.

In conventional arrangements, the static configuration data is defined during a fitting session and is stored in non-volatile memory of the cochlear implant during the fitting session. That is, conventional arrangements require non-volatile memory (i.e., permanent storage) in the cochlear implant 104, as well as the presence of an RF backchannel for the sound processor to detect the state of the cochlear implant. However, using the techniques presented herein, the need for the non-volatile memory of the cochlear implant, as well as the RF backchannel, can be eliminated.

More specifically, in accordance with the embodiments presented herein, the static configuration data is stored in the external sound processing unit 106 (i.e., not in the cochlear implant 104) and the static configuration data is streamed together with the dynamic stimulation data over the wireless channel 110 to the power button 108 for subsequent forwarding to the cochlear implant 104. Since the static configuration data is predetermined and recipient-specific, the static configuration data is split in multiple discrete segments that are transmitted in a continuously repeated pattern. Because the static configuration data is streamed over the wireless channel, there is no need for a non-volatile memory in the cochlear implant 104 to store the static configuration. This simplifies the hardware of the cochlear implant 104 and, potentially, enables interoperability between external components and cochlear implants from different manufacturers. Moreover, since the static configuration data is continuously repeated, the cochlear implant can start decoding the data at any point in time. The sound processing unit 106 does not need to know when the cochlear implant 104 is present before transmission of the static configuration data, which further simplifies the system design.

In general, static configuration data is data which is recipient-specific, but does not vary over time, while dynamic data is the data that varies over time and is defined by the acoustic input (sound signals). Static configuration data and dynamic stimulation data streamed over an isochronous wireless communication channel, such as wireless channel 110, are collectively and generally referred to herein as "streaming stimulation data."

FIG. 2 is a schematic diagram illustrating the basic standard wireless packet structure/framework into which streaming stimulation data may be encoded/mapped in accordance with embodiments of present invention. In FIG. 2, the wireless packet 140 comprises an optional header 142, a payload 144 of isochronous data, and an error correction field/trailer 146. The payload 144 may include 8 bit, 16 bit, 32 bit, etc. formatted data. The error correction field 146 may include Cyclic Redundancy Check (CRC) information.

FIGS. 3A-3N are a series of schematic diagrams illustrating the encoding of the streaming stimulation data into the structure of wireless packet 140. More specifically, FIGS. 3A-3N illustrate a series of payloads 144(A)-144(N) that may be transmitted as payloads in a series of wireless packets having the format generally shown in FIG. 2.

As first shown in FIG. 3A, the streaming stimulation data 148(A) includes a first segment 152(A) (i.e., segment 1) of the static configuration data and dynamic stimulation data 154(A) (i.e., dynamic data 1). The dynamic stimulation data 154(A) is stimulation data that is generated from a first set of one or more sound signals. The payload 144(A) may also include an optional header 150(A) and an optional error correction field 156(A) with, for example, CRC information.

Since dynamic stimulation data is generated based on the sound inputs, the dynamic stimulation data will vary from packet to packet on the wireless channel. As such, FIG. 3B illustrates streaming stimulation data 148(B) that is encoded into payload 144(B). The streaming stimulation data 148(B) includes a second segment 152(B) (i.e., segment 2) of the static configuration data and dynamic stimulation data 154(B) (i.e., dynamic data 2) generated from a second set of one or more sound signals. The payload 144(B) also includes an optional header 150(B) and an optional error correction field 156(B).

As noted, the static configuration data is divided into a plurality of segments for wireless transmission from the sound processing unit 106 to the power button 108. In the embodiment of FIGS. 3A-3N, there are M segments of the static configuration data and FIG. 3M represents the payload 144(M) of the $M^{th}$ wireless packet. The payload 144(M) illustrates streaming stimulation data 148(M) that includes the last segment 152(M) (i.e., the $M^{th}$ segment) of the static configuration data and dynamic stimulation data 154(M) (i.e., dynamic data M) generated from an $M^{th}$ set of one or more sound signals. The payload 144(M) also includes an optional header 150(M) and an optional error correction field 156(M).

FIG. 3N represents the payload 144(N) of the $N^{th}$ wireless packet that includes streaming stimulation data 148(N). Since there are only M segments of the static configuration data, the segments of the static configuration data begin repeating after the $M^{th}$ packet. That is, the payload 144(N) includes the first segment 152(A) of the static configuration data (i.e., a retransmission of segment 1). However, payload 144(N) includes dynamic stimulation data 154(N) (i.e., dynamic stimulation data N) generated from an $N^{th}$ set of one or more sound signals. The payload 144(N) also includes an optional header 150(N) and an optional error correction field 156(N). In other words, payload 144(N) includes a repeat of the static configuration data of FIG. 3A, but also includes newly generated dynamic stimulation data. The segments of stimulation data are continually repeated, in order, during operation of the wireless channel 110.

FIGS. 3A-3N illustrate exemplary arrangements for wireless packet payloads in accordance with examples presented herein. It is to be appreciated that the static data segments, dynamic data, etc. inside the exemplary data packet structure may be reordered and/or additional elements may be added (e.g., encryption, session keys, etc.).

FIG. 4 is a functional block diagram illustrating elements of the sound processing unit 106 and power button 108. In general, FIG. 4 illustrates only the elements of the sound processing unit 106 and power button 108 related to the transfer of isochronous stimulation data over a standardized wireless channel in accordance with the embodiments presented herein. Other elements of the sound processing unit 106 and power button 108 (e.g., batteries, magnets, etc.), have been omitted from FIG. 4 for ease of illustration.

The elements of sound processing unit 106 shown in FIG. 4 include a sound input element 160, a sound processor 162, and a wireless transceiver 164. The wireless transceiver 164 includes a codec 166 that comprises a compression module 168 and an isochronous encoder 170. The elements of power button 108 shown in FIG. 4 include a wireless transceiver 172, an RF encoder (coil driver) 174, and an RF coil 176. The wireless transceiver 172 includes a codec 178 that comprises an isochronous decoder 180 and a decompression module 182.

In operation, sound processor 162 converts sound information (e.g., inputs received from sound input element 160) into encoded data signals that control the timing and intensity of current stimulation pulses for delivery by cochlear implant 104. As noted above, the encoded data signals generated by the sound processor 162 are referred to herein as dynamic stimulation data that is generally represented in FIG. 4 by arrow 165. The sound processor 162 executes one or more sound processing/coding strategies to generate the dynamic stimulation data 165. Sound coding strategies that may be executed by the sound processor 162 include, but are not limited to, Continuous Interleaved Sampling (CIS), Spectral PEAK Extraction (SPEAK), Advanced Combination Encoders (ACE), Fundamental Asynchronous Stimulus Timing (FAST), Simultaneous Analog Stimulation, MPS, Paired Pulsatile Sampler, Quadruple Pulsatile Sampler, Hybrid Analog Pulsatile), n-of-m, etc.

In one specific example, the sound processor 162 uses an ACE strategy to process a first set of one or more sound signals that are generally represented in FIG. 4 by arrow 161. The illustrative ACE strategy generates eight (8) stimuli at a rate of 900 Hertz (Hz), where each stimulus is defined in the dynamic stimulation data 165 by the stimulus channel and the stimulus amplitude. In this example, the static configuration data includes pulse timing information (e.g., pulse width, pulse gap, and inter-stimulus gap), stimulation mode information (e.g., monopolar 1 (MP1), monopolar 2 (MP2), Monopolar 1+2 (MP1+2), etc.), and channel-to-electrode mapping information. The stimulation configuration data is generally represented in FIG. 4 by arrow 167.

As shown in FIG. 4, the static configuration data 167 and the dynamic stimulation data 165 generated from sound signals 161 are both provided to the codec 166 in the wireless transceiver 164. The static configuration data 167 is provided directly to the encoder 170, but the dynamic stimulation data 165 is provided to compression module 168 for compression. The compression module 168 generates compressed dynamic stimulation data. The compressed dynamic stimulation data, which is generally represented in FIG. 4 by arrow 169, is provided to the isochronous encoder 170. The isochronous encoder 170 is configured to encode the compressed dynamic stimulation data 169 and the static configuration data 167 for transmission within the standardized framework (i.e., packet/frame format) provided for isochronous wireless channel 110.

Figure 5:
FIG. 5 is a table illustrating wireless packet encoding in accordance with an example embodiment of the present invention.

FIG. 5 is a table 200 illustrating the content of a series of wireless frames transmitted on wireless channel 110 in accordance with embodiments presented herein. More specifically, isochronous wireless channels may have different frame formats, but will be subject to various maximum bit rates. In the example of FIG. 5, the isochronous wireless channel 110 has a maximum bitrate of 96 kbps and may use, for example, data transmitted at a rate of 1 kHz in blocks of 12 bytes. As such, the compressed dynamic stimulation data is limited to less than approximately 96 kbps.

For efficiency, embodiments of the present invention adapt the stimulation rate to match the frame rate, meaning that, in one example, eight (8) stimuli need to be transferred in each packet/frame. In a typical ACE strategy, each set of stimuli comprises zero (0) to eight (8) stimuli on unique channels in a fixed order. This means that the stimulus channels can be encoded in twenty-two (22) bits, where each bit indicates if a channel is present. In addition, the stimulus amplitudes can be encoded in 8 bits. As noted above, the static configuration data comprises 3 timing parameters, 1 stimulation mode, and 22 electrode numbers, which is rounded to 32 bytes. As shown in FIG. 5, the stimulus channels and amplitudes will occupy 11 bytes of the frame (bytes 1-11), which means there is one byte left in the frame (byte 0) that may be used to transfer the static configuration data in a serialized manner. As such, each frame includes 1 of the 32 bytes of static configuration data and, after 32 frames, the static configuration data is re-transmitted 1 byte at a time.

In accordance with embodiments presented herein, to synchronize the decoding of the static configuration data, one spare bit of the channel bitmap will be used to indicate the first frame of a block of 32 frames (i.e., to indicate the start of a new static configuration data cycle). In FIG. 5, this synchronization bit is encoded in byte 0 of frame 0. The static configuration data may also include its own CRC to protect against missing frames.

In summary, each line in the table 200 of FIG. 5 represents a frame of 12 bytes, where each frame encodes: stimulus channels 1-22, which are encoded as bits in the first 3 bytes of the frame (i.e., bytes 0-2); stimulus levels, which are encoded in the next 8 bytes (i.e., bytes 3-10); and a segment (0-31) of the static configuration data, which is encoded in the last byte (i.e., byte 11).

Returning to FIG. 4, as described above, the isochronous encoder 170 generates at least one wireless frame 184 that is transmitted over the wireless channel 110 to the power button 108. The wireless frame 184 is received at the wireless transceiver 172 for processing by the codec 178. In particular, the isochronous decoder 180 is configured to decode wireless frame 185 to extract the compressed dynamic stimulation data 169 and the segment of the static configuration data 167 encoded in the wireless frame. FIG. 4 illustrates that the recovered compressed dynamic stimulation data 169 is provided to the decompression module 182. The decompression module 182 is configured to recover the original dynamic stimulation data 165. FIG. 4 also illustrates that the segment of static configuration data, generally represented in FIG. 4 by arrow 177, is provided to the RF encoder 174. The RF encoder 174 includes components configured to modulate the RF carrier so as to encode the segment of static configuration data 174 and the dynamic stimulation data 165 within an electromagnetic field that propagates from RF coil 176. In other words, RF encoder 174 is configured to transmit the segment of static configuration data 174 and the dynamic stimulation data 165 to cochlear implant 104 (FIG. 1) over a closely coupled RF channel.

Embodiments of the present invention have been primarily described herein with reference to the simultaneous streaming of segments of static configuration data and dynamic stimulation data over an isochronous wireless channel formed between a BTE sound processing unit and a power coil. However, it is to be appreciated that embodiments presented herein may be used to simultaneous stream static configuration data and dynamic stimulation data between on or more other devices.

For example, FIG. 6 is a schematic diagram illustrating a system 300 in which a mobile consumer device (mobile device) 302 operates to simultaneously stream static configuration data and dynamic stimulation data to a power button, such as power button 108 described above. The mobile device 302 may be, for example, a mobile phone, personal digital assistant (PDA), tablet computer, etc. In accordance with examples presented herein, the mobile device 302 includes a sound processor that is configured to generate dynamic stimulation data, as described above. The mobile device 302 also includes memory in which static configuration data for cochlear implant 104 is stored, and a wireless transceiver for wireless communication with, for example, the power button 108 or other devices. The wireless transceiver in the mobile device 302 may have an arrangement that is similar to that of wireless transceiver 164 (FIG. 4) so as to form an isochronous wireless channel 310 with power button 108 and to simultaneously stream the stored static configuration data with dynamic stimulation data.

Again, the embodiment of FIG. 6 is illustrative and other arrangements are possible. For example, in an alternative arrangement a cochlear implant is configured with a standardized wireless transceiver and is able to receive simultaneously streamed static configuration data and dynamic stimulation data directly from an external device. For example, a sound processing unit could form an isochronous wireless channel directly with a cochlear implant. Such a sound processing unit could be a behind-the-ear processing unit or a "button" or coil sound processing unit. A coil sound processing unit is a component in which the sound processor, external coil arrangement, and external magnet are all disposed within (or adjacent to) the same housing configured to be worn at the same location as where an external coil is traditionally located. A coil sound processing unit may be configured to transfer of isochronous stimulation data over a standardized audio link with a cochlear implant that comprises a wireless transceiver.

FIG. 7 is a flowchart of a method 250 in accordance with embodiments presented herein. Method 250 begins at 255 where a first component of an implantable medical device system generates dynamic stimulation data that is representative of current stimulation for delivery to a recipient of the implantable medical device system. At 260, the first component obtains static configuration data and, at 265, the first component encodes the dynamic stimulation data and a first segment of the static configuration data into an isochronous wireless packet. At 270, the first component wirelessly transmits the wireless packet comprising the dynamic stimulation data and the first segment of static configuration data over an isochronous wireless channel to a second component of the implantable medical device system.

Embodiments of the present invention have been primarily described with reference to specification configurations of an isochronous wireless channel between a sound processing unit and a power button and/or implant for streaming dynamic stimulation data with static configuration data. It is to be appreciated that other embodiments may utilize an isochronous wireless channel between other devices. For example, an isochronous channel may be formed between a mobile computing device (e.g., mobile phone, tablet computer, etc.) or other consumer electronic device and a sound processing unit, power button, or implant. In examples in which the mobile computing device generates and streams dynamic stimulation data (with or without static configuration data) to a sound processing unit, the sound processing unit streams the dynamic stimulation data received from the mobile computing device, possibly along other dynamic stimulation data generated at the sound processing unit, to the power button or implant. Again, this dynamic stimulation data is streamed with static configuration data.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
receiving one or more sound signals at one or more sound input elements of a first component of an cochlear implant system;
generating, at a sound processor of the first component, dynamic stimulation data based on the sound signals, wherein the dynamic stimulation data is representative of current stimulation for delivery to a recipient of the cochlear implant system;
obtaining, from memory in the first component, static configuration data defining one or more recipient-specific parameters for control of the current stimulation;
encoding the dynamic stimulation data and a segment of the static configuration data into an isochronous wireless packet; and
wirelessly transmitting the isochronous wireless packet comprising the dynamic stimulation data and the segment of static configuration data over an isochronous wireless channel to a second component of the cochlear implant system.

2. The method of claim 1, further comprising:
compressing the dynamic stimulation data to generate compressed dynamic stimulation data; and
encoding the compressed dynamic stimulation data and the segment of static configuration data into the isochronous wireless packet.

3. The method of claim 1, wherein the first and second components are both external components of the cochlear implant system, and further comprising:
decoding the wireless packet at the second external component to extract the dynamic stimulation data and the segment of static configuration data; and
transmitting the dynamic stimulation data and the segment of static configuration data over a closely-coupled radio-frequency (RF) link to an implantable component.

4. The method of claim 3, further comprising:
generating, at the implantable component, current stimulation pulses based on the dynamic stimulation data and in accordance with at least the segment of static configuration data; and
delivering the current stimulation pulses to the recipient of the cochlear implant system to evoke perception of the sound signals by the recipient.

5. The method of claim 1, wherein the first component is an external component of the cochlear implant system and the second component is an implantable component of the cochlear implant system, further comprising:
decoding the wireless packet at the implantable component to extract the dynamic stimulation data and the segment of static configuration data; and
generating, at the implantable component, current stimulation pulses based on the dynamic stimulation data and in accordance with at least the segment of static configuration data; and
delivering the current stimulation pulses to the recipient of the cochlear implant system to evoke perception of the sound signals by the recipient.

6. The method of claim 1, further comprising:
generating the dynamic stimulation data based on the sound signals so as to represent the intensity and location of current stimulation pulses that, when delivered by cochlear implant, will evoke perception of the sound signals by the recipient.

7. The method of claim 1, wherein wirelessly transmitting the isochronous wireless packet over an isochronous wireless channel to a second component of the cochlear implant system comprises:
wirelessly transmitting the isochronous wireless packet over an isochronous wireless channel operated in accordance with a short-range wireless standard.

8. The method of claim 7, wherein wirelessly transmitting the isochronous wireless packet over an isochronous wireless channel operated in accordance with a short-range wireless standard comprises:
wirelessly transmitting the isochronous wireless packet over an isochronous wireless channel defined by a standardized communication protocol.

9. The method of claim 1, wherein encoding the dynamic stimulation data and a segment of the static configuration data into an isochronous wireless packet comprises:
encoding, in a header of the isochronous wireless packet, an indication that the isochronous wireless packet includes dynamic stimulation data.

10. The method of claim 1, wherein obtaining the static configuration data comprises:
the static configuration data obtaining one or more of pulse timing information, stimulation mode information, and channel-to-electrode mapping information controlling the current stimulation for delivery to a recipient.

11. The method of claim 1, further comprising:
encrypting the isochronous wireless packet before wirelessly transmitting the isochronous wireless packet over the isochronous wireless channel.

12. The method of claim 1, further comprising:
generating a plurality of sets of dynamic stimulation data based on the sound signals, segmenting the static configuration data into a plurality of discrete static configuration data segments; and
wirelessly streaming each of the plurality of static configuration data segments with one of the plurality of sets of dynamic stimulation data over the isochronous channel in a serialized and repetitive manner.

13. The method of claim 12, further comprising:
compressing each of the plurality of sets of dynamic stimulation data before wirelessly streaming of the plurality of sets of dynamic stimulation data over the isochronous channel.

14. The method of claim 12, wherein the plurality of static configuration data segments and the plurality of sets of dynamic stimulation are wirelessly streamed from a first external component to a second external component of the cochlear implant system, and wherein the method further comprises:
extracting, from the isochronous channel, each of the sets of dynamic stimulation data and the plurality of static configuration data segments at the second external component; and
transmitting each of the sets of dynamic stimulation data and the plurality of static configuration data segments at the second external component over a closely-coupled radio-frequency (RF) link to an implantable component of the cochlear implant system.

15. A cochlear implant system, comprising:
a first component, comprising:
one or more sound input elements configured to receive one or more sound signals;
non-volatile memory configured to store static configuration data defining one or more recipient-specific parameters for control of the current stimulation;
a sound processor of configured to generate dynamic stimulation data based on the sound signals, wherein the dynamic stimulation data is representative of current stimulation for delivery to a recipient of the cochlear implant system; and
a wireless transceiver configured to obtain, from the non-volatile memory, the static configuration data, encode the dynamic stimulation data and a segment of the static configuration data into an isochronous wireless packet, and wireless transmit the isochronous wireless packet comprising the dynamic stimulation data and the segment of static configuration data over an isochronous wireless channel to a second component of the cochlear implant system.

16. The cochlear implant system of claim 15, wherein the wireless transceiver is configured to:
compress the dynamic stimulation data to generate compressed dynamic stimulation data; and
encode the compressed dynamic stimulation data and the segment of static configuration data into the isochronous wireless packet.

17. The cochlear implant system of claim 15, wherein the first and second components are both external components of the cochlear implant system, and wherein the second component comprises a wireless transceiver configured to:
decode the wireless packet at the second external component to extract the dynamic stimulation data and the segment of static configuration data; and
transmit the dynamic stimulation data and the segment of static configuration data over a closely-coupled radio-frequency (RF) link to an implantable component.

18. The cochlear implant system of claim 15, wherein the first component is an external component of the cochlear implant system and the second component is an implantable component of the cochlear implant system, and wherein the second component comprises a wireless transceiver configured to decode the wireless packet at the implantable component to extract the dynamic stimulation data and the segment of static configuration data.

19. The cochlear implant system of claim 15, wherein the sound processor is configured to generate the dynamic stimulation data based on the sound signals so as to represent the intensity and location of current stimulation pulses that, when delivered by cochlear implant system, will evoke perception of the sound signals by the recipient.

20. The cochlear implant system of claim 15, wherein to wirelessly transmit the isochronous wireless packet over an isochronous wireless channel to a second component of the cochlear implant system, the wireless transceiver is configured to wirelessly transmit the isochronous wireless packet over an isochronous wireless channel operated in accordance with a short-range wireless standard.

21. The cochlear implant system of claim 15, wherein to encode the dynamic stimulation data and a segment of the static configuration data into an isochronous wireless packet, the wireless transceiver is configured to encode, in a header of the isochronous wireless packet, an indication that the isochronous wireless packet includes dynamic stimulation data.

22. The cochlear implant system of claim 15, wherein the static configuration data comprises one or more of pulse timing information, stimulation mode information, and channel-to-electrode mapping information controlling with the current stimulation for delivery to a recipient.

23. The cochlear implant system of claim 15, wherein the wireless transceiver is configured to encrypt the isochronous wireless packet before wirelessly transmitting the isochronous wireless packet over the isochronous wireless channel.

\* \* \* \* \*